(12) United States Patent
McPherson

(10) Patent No.: US 9,987,072 B2
(45) Date of Patent: Jun. 5, 2018

(54) SYSTEM AND METHOD FOR DETECTING A FAULT IN A CAPACITIVE RETURN ELECTRODE FOR USE IN ELECTROSURGERY

(75) Inventor: James W. McPherson, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 1341 days.

(21) Appl. No.: 12/401,428

(22) Filed: Mar. 10, 2009

(65) Prior Publication Data

US 2009/0234353 A1 Sep. 17, 2009

Related U.S. Application Data

(60) Provisional application No. 61/037,210, filed on Mar. 17, 2008.

(51) Int. Cl.
*A61B 18/04* (2006.01)
*A61B 18/12* (2006.01)
*A61B 18/16* (2006.01)

(52) U.S. Cl.
CPC .......... *A61B 18/1233* (2013.01); *A61B 18/16* (2013.01); *A61B 2018/1253* (2013.01); *A61B 2018/167* (2013.01)

(58) Field of Classification Search
CPC . A61B 18/1233; A61B 18/1206; A61B 18/12; A61B 18/04; A61B 18/00;
(Continued)

(56) References Cited

U.S. PATENT DOCUMENTS 3,979,897 A * 9/1976 Vogelsberg .......... G01R 31/022
57/264
4,188,927 A 2/1980 Harris
(Continued)

FOREIGN PATENT DOCUMENTS

CA 1219642 3/1987
DE 3206947 9/1983
(Continued)

OTHER PUBLICATIONS

U.S. Appl. No. 10/609,946, filed Jun. 30, 2003.
(Continued)

*Primary Examiner* — Edelmira Bosques

(57) ABSTRACT

An electrosurgical system includes an electrosurgical generator, a capacitive return pad, a phase detection component, and a control component. The electrosurgical generator is configured to generate electrosurgical energy. The capacitive return pad has at least one capacitive return electrode operatively coupled to the electrosurgical generator and is configured to provide a return path for the electrosurgical energy. The phase detection component is configured to determine a phase difference between the current and the voltage of the electrosurgical energy. The control component is in operative communication with the phase detection component and is configured to receive the determined phase difference from the phase detection component. The control component is configured to detect a fault in the capacitive return pad by utilizing the determined phase difference.

12 Claims, 5 Drawing Sheets

(58) Field of Classification Search
CPC . A61B 18/16; A61B 18/14; A61B 2018/1253; A61B 208/1246; A61B 2018/167
USPC .......................... 606/31, 32, 34, 35, 38, 41
See application file for complete search history.

(56) References Cited

U.S. PATENT DOCUMENTS

| | | | |
|---|---|---|---|
| 4,200,104 A | | 4/1980 | Harris |
| 4,231,372 A | | 11/1980 | Newton |
| 4,416,276 A | | 11/1983 | Newton et al. |
| 4,416,277 A | | 11/1983 | Newton et al. |
| 4,844,063 A | | 7/1989 | Clark et al. |
| 4,848,335 A | | 7/1989 | Manes |
| 5,160,334 A | | 11/1992 | Billings et al. |
| 5,312,401 A | * | 5/1994 | Newton ............. A61B 18/1233 606/35 |
| 5,372,596 A | * | 12/1994 | Klicek et al. .................. 606/35 |
| 5,390,382 A | | 2/1995 | Hannant et al. |
| 5,558,671 A | * | 9/1996 | Yates ............................... 606/38 |
| 5,632,280 A | | 5/1997 | Leyde et al. |
| 5,688,269 A | | 11/1997 | Newton et al. |
| 5,718,719 A | | 2/1998 | Clare et al. |
| 5,830,212 A | * | 11/1998 | Cartmell ............ A61B 18/1233 128/908 |
| 5,936,536 A | * | 8/1999 | Morris .......................... 340/647 |
| 6,275,786 B1 | | 8/2001 | Daners |
| 6,409,722 B1 | | 6/2002 | Hoey et al. |
| 6,537,272 B2 | | 3/2003 | Christopherson et al. |
| 6,736,810 B2 | | 5/2004 | Hoey et al. |
| 7,004,727 B2 | * | 2/2006 | Kline et al. ...................... 417/46 |
| 7,422,589 B2 | | 9/2008 | Newton et al. |
| 2001/0001314 A1 | * | 5/2001 | Davison et al. ................ 606/41 |
| 2005/0113817 A1 | * | 5/2005 | Isaacson ................ A61B 18/16 606/32 |
| 2006/0041251 A1 | | 2/2006 | Odell et al. |
| 2006/0041252 A1 | | 2/2006 | Odell et al. |
| 2007/0074719 A1 | * | 4/2007 | Danek et al. ............. 128/200.24 |
| 2008/0039831 A1 | * | 2/2008 | Odom et al. ..................... 606/34 |
| 2008/0058799 A1 | * | 3/2008 | Kadziauskas et al. ......... 606/41 |
| 2008/0071263 A1 | * | 3/2008 | Blaha ................. A61B 18/1233 606/35 |
| 2008/0281311 A1 | * | 11/2008 | Dunning ................ A61B 18/16 606/32 |
| 2009/0234352 A1 | * | 9/2009 | Behnke et al. ................. 606/35 |

FOREIGN PATENT DOCUMENTS

| | | |
|---|---|---|
| DE | 3544443 | 6/1987 |
| DE | 4238263 | 5/1993 |
| DE | 4231236 | 3/1994 |
| DE | 19717411 | 11/1998 |
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 836868 | 4/1998 |
| EP | 0930048 | 7/1999 |
| EP | 1051949 | 11/2000 |
| EP | 1076350 | 2/2001 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| EP | 1 994 905 A | 11/2008 |
| FR | 2276027 | 6/1974 |
| FR | 2516782 | 5/1983 |
| GB | 2054382 | 2/1981 |
| GB | 2374532 | 10/2002 |
| JP | 200092693 * | 3/2000 |
| WO | WO 93/00862 A | 1/1993 |
| WO | WO 00/65993 | 11/2000 |
| WO | WO 05/087124 | 9/2005 |
| WO | WO 2005/115262 | 12/2005 |
| WO | WO 2008/009385 | 1/2008 |

OTHER PUBLICATIONS

U.S. Appl. No. 11/900,190, filed Sep. 10, 2007.
U.S. Appl. No. 12/396,814, filed Mar. 3, 2009.
U.S. Appl. No. 12/395,812, filed Mar. 2, 2009.
U.S. Appl. No. 12/364,624, filed Feb. 3, 2009.
U.S. Appl. No. 12/355,281, filed Jan. 16, 2009.
U.S. Appl. No. 12/401,428, filed Mar. 10, 2009.
U.S. Appl. No. 12/407,008, filed Mar. 19, 2009.
Boyles, Walt; "Instrumentation Reference Book", 2002; Butterworth-Heinemann ; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
International Search Report PCT/US2004/004196 dated Oct. 4, 2007.
European Search Report for Appln. No. EP 09 00 3809 completed Jun. 10, 2009.

* cited by examiner

SYSTEM AND METHOD FOR DETECTING A FAULT IN A CAPACITIVE RETURN ELECTRODE FOR USE IN ELECTROSURGERY

PRIORITY

This application claims the benefit of priority to U.S. Provisional Application Ser. No. 61/037,210 entitled "SYSTEM AND METHOD FOR DETECTING A FAULT IN A CAPACITIVE RETURN ELECTRODE FOR USE IN ELECTROSURGERY" filed Mar. 17, 2008 by James McPherson, which is incorporated by reference herein.

BACKGROUND

Technical Field

The present disclosure relates to electrosurgery. More particularly, the present disclosure relates to a system and method for detecting a fault in a capacitive return electrode for use in electrosurgery.

Description of Related Art

Electrosurgery is the application of electricity and/or electromagnetic energy to cut or modify biological tissue during a surgical procedure. Generally, electrosurgery utilizes an electrosurgical generator, an active electrode, and a return electrode. The electrosurgical generator generates an electromagnetic wave (referred to herein as "electrosurgical energy"), typically above 100 kilohertz, between the active and return electrodes when applied to tissue. The electromagnetic wave created therebetween dissipates energy as heat as it travels between the electrodes. The electrosurgical energy usually has a frequency above 100 kilohertz to avoid muscle and/or nerve stimulation.

During electrosurgery, current generated by the electrosurgical generator is conducted through the patient's tissue disposed between the two electrodes. The current causes the tissue to heat up as the electromagnetic wave overcomes the tissue's impedance. Although many other variables affect the total heating of the tissue, usually more current density directly correlates to increased heating. The electrosurgical energy is typically used for cutting, dissecting, ablating, coagulating, and/or sealing tissue.

The two basic types of electrosurgery employed are monopolar and bipolar electrosurgery; however, both types use an "active" and a "return" electrode. In bipolar electrosurgery, the surgical instrument includes an active electrode and a return electrode on the same instrument or in very close proximity, usually causing current to flow through a smaller amount of tissue. In monopolar electrosurgery, the return electrode is located elsewhere on the patient's body and is usually not part of the electrosurgical instrument itself. In monopolar electrosurgery, the return electrode is part of a device usually referred to as a return pad.

The return pad may have one or more return electrodes. The return electrodes are typically in the form of pads adhesively adhered to the patient and are placed remotely from the active electrode to carry the current back to the generator. The return electrodes usually have a large patient contact surface area to minimize heating at that site since the smaller the surface area, the greater the current density and the greater the intensity of the heat. That is, the area of the return electrode that is adhered to the patient is important because it is the current density of the electrical signal that heats the tissue. A larger surface contact area is desirable to reduce localized heat intensity. Return electrodes are typically sized based on assumptions of the maximum current utilized during a particular surgical procedure and the duty cycle (i.e., the percentage of time the generator is on). The first types of return electrodes were in the form of large metal plates covered with conductive jelly. Later, adhesive electrodes were developed with a single or dual-split metal foil covered with conductive jelly or conductive adhesive.

Another type of return pad is the capacitive return pad. A capacitive return pad has one or more capacitive return electrodes. A capacitive return electrode usually includes two layers of metal foil as mentioned above with the addition of a dielectric material disposed in between the metal foils. The dielectric material is designed to be positioned between the top and bottom metal foils. The capacitive return electrode allows electrosurgical energy of sufficient frequency to pass through the capacitance of the pad and the patient but prevents DC or very low frequencies from passing through the return pad. The addition of the dielectric material generally causes the heat to be more evenly distributed throughout the capacitive return pad.

The effects of the electrosurgical energy is also affected by other factors, including the patient's age, weight, the type of tissue being modified, and the desired tissue effect. Different tissue effects occur by varying the voltages, currents, duty cycle, and frequencies used.

SUMMARY

The present disclosure relates to electrosurgery, and, in particular, to a system and method for detecting a fault in a capacitive return electrode for use in electrosurgery, e.g. a fault from a pinhole defect, which shorts out the capacitance causing excessive heating at that point.

In an aspect of the present disclosure, an electrosurgical system includes an electrosurgical generator, a capacitive return pad, a phase detection component, and a control component. The electrosurgical generator is configured to generate electrosurgical energy. The capacitive return pad has at least one capacitive return electrode operatively coupled to the electrosurgical generator and provides a return path for the electrosurgical energy. The phase detection component can determine a phase difference between the current and the voltage of the electrosurgical energy. The control component is in operative communication with the phase detection component and receives the determined phase difference therefrom. The control component can detect a fault in the capacitive return pad (e.g., a fault caused from a pinhole defect) by utilizing the determined phase difference. The phase detection component and/or the control component are at least partially implemented by an operative set of processor executable instructions configuration for execution by at least one processor.

The at least one capacitive return electrode can include a plurality of capacitive return electrodes. Additionally or alternatively, the control component can disconnect a faulted capacitive return electrode of the plurality of capacitive return electrodes from the electrosurgical energy when the fault is detected. The control component detects the fault by detecting a change in the phase difference during electrosurgery and/or by detecting an increase in the phase difference during electrosurgery.

In one embodiment, the phase detection component includes one or more of an analog-to-digital converter, an analog multiplier, a zero crossing detector, a digital signal processor, a phase-locked-loop circuit, a sample-and-hold circuit, a phase-to-voltage converter having an XOR logic gate, a sequential-phase detector, and/or a current transformer.

In another embodiment of the present disclosure, the electrosurgical energy includes an interrogation signal and the determined phase difference is a phase difference between the current and the voltage of the interrogation signal. The determined phase difference is compared to a predetermined threshold to detect the fault. In another embodiment, the electrosurgical system includes a database configured to calculate the predetermined threshold. The database calculates the predetermined threshold by utilizing at least one parameter, e.g., a length of a cable, an impedance of the cable, a characteristic impedance of the cable, a resistance of the cable, an inductance of the cable, a capacitance of the cable, an age of a patient, a weight of the patient, a height of the patient, a model number of the capacitive return pad, a RFID interrogation of the cable, and/or another RFID interrogation of the capacitive return pad.

In another embodiment of the present disclosure, the control component raises a flag when the fault is detected. The flag may be a software flag and/or a hardware flag. For example, the software flag may be a software interrupt and the hardware flag may be a hardware interrupt.

In yet another embodiment of the present disclosure, a method is disclosed which detects a fault in a capacitive return pad and includes the steps of providing an electrosurgical system and activating the electrosurgical system. The method includes the step of determining the phase difference between the current and the voltage of the electrosurgical energy. The method may also include the step of replacing the capacitive return pad in response to the detected fault. Additionally or alternatively, capacitive return pad may include a plurality of capacitive return electrodes, and the method may further include the step of disconnecting a faulted capacitive return electrode of the plurality of capacitive return electrodes from the electrosurgical energy when the fault is detected.

In another embodiment, the electrosurgical energy includes an interrogation signal and the method determines a phase difference such that the determined phase difference is a phase difference between the current and the voltage of the interrogation signal; and the method may further include the step of generating the interrogation signal. The method may also include comparing the determined phase difference to a predetermined threshold to detect the fault and/or detecting a change in the phase difference during electrosurgery to detect the fault. In another embodiment, the method includes raising a flag when the fault is detected. The flag may include a software flag and/or a hardware flag.

BRIEF DESCRIPTION OF THE DRAWINGS

These and other advantages will become more apparent from the following detailed description of the various embodiments of the present disclosure with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
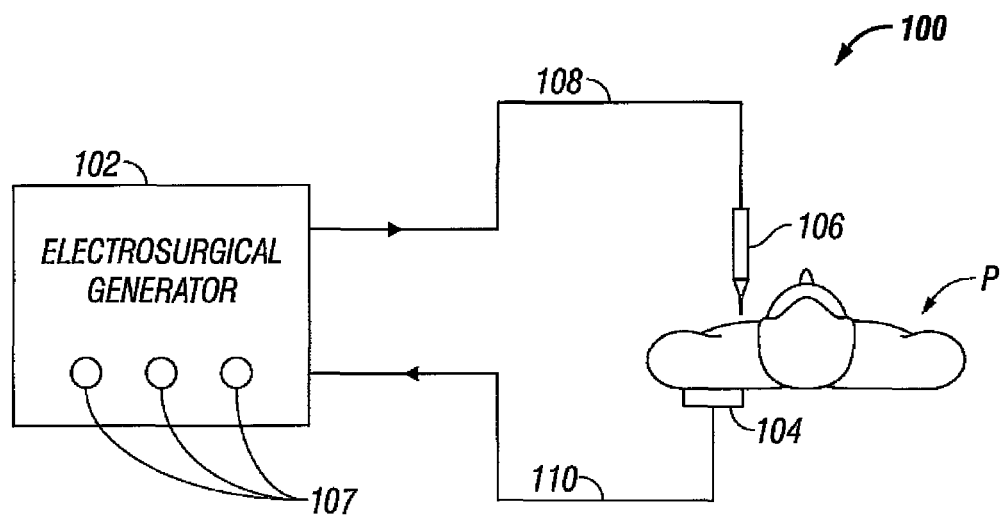
FIG. 1 is a block diagram of an electrosurgical system having a capacitive return pad in accordance with the present disclosure.

Referring to the drawings, FIG. 1 is a block diagram illustration of an electrosurgical system 100 according to an embodiment of the present disclosure. Electrosurgical system 100 includes electrosurgical generator 102 that can detect a fault in capacitive return pad 104. Electrosurgical system 100 also includes an electrosurgical instrument 106 having one or more active electrodes for treating tissue of patient P. Electrosurgical instrument 106 is a monopolar instrument and may include active electrodes designed for a wide variety of electrosurgical procedures (e.g., electrosurgical cutting, ablation, etc.). Electrosurgical energy is supplied to electrosurgical instrument 106 by electrosurgical generator 102 via cable 108, which is connected to an active output terminal, allowing instrument 106 to coagulate, ablate and/or otherwise treat tissue. The electrosurgical energy is returned to electrosurgical generator 102 through capacitive return pad 104 via cable 110 after passing through patient P.

Electrosurgical system 100 includes a plurality of return capacitive return pads 104 that are arranged to minimize the chances of tissue damage by maximizing the overall contact area with the patient P. Electrosurgical generator 102 and the capacitive return pad 104 are typically configured for monitoring so-called "tissue-to-patient" contact to ensure that sufficient contact exists therebetween to further minimize chances of tissue damage. Capacitive return pad 104 may include one or more capacitive return electrodes that may have additional hardware, software, firmware, circuitry, and the like to disconnect a faulted capacitive return electrode from the electrosurgical energy generated by electrosurgical generator 102 (discussed in more detail below). Additionally or alternatively, electrosurgical generator 102 may include hardware, software, firmware, circuitry, and/or the like to disconnect a faulted capacitive return electrode.

The electrosurgical generator 102 includes input controls 107 (e.g., buttons, activators, switches, touch screen, etc.) for controlling electrosurgical system 100. In addition, electrosurgical generator 102 includes one or more display screens (not shown) for providing the user with a variety of output information (e.g., intensity settings, treatment complete indicators, etc.). The controls 107 allow the user (e.g., a surgeon, nurse, or technician) to adjust the electrosurgical energy, e.g., power, waveform, duty cycle, voltage, current, frequency, and/or other parameters to achieve the desired electrosurgical energy characteristics suitable for a particular task (e.g., coagulating, tissue sealing, intensity setting, etc.). The electrosurgical instrument 106 may also include one or more input controls (not shown) that may be redundant with certain input controls of electrosurgical generator 102. Placing the input controls on the electrosurgical instrument 106 can allow for easier and faster modification of the electrosurgical energy during the surgical procedure without requiring interaction with electrosurgical generator 102.

Figure 2A:
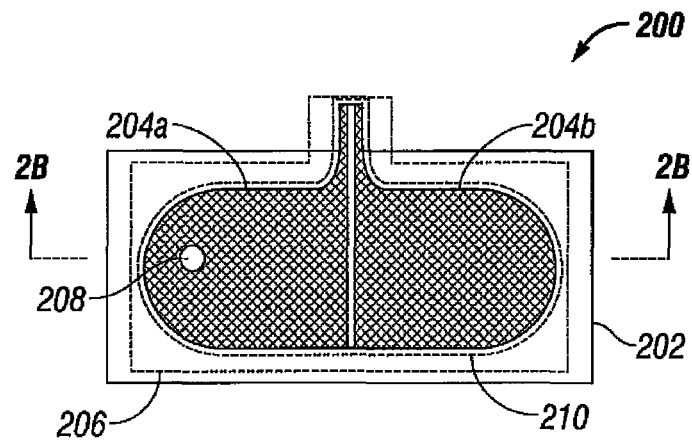
FIG. 2A is a bottom view of a capacitive return pad having two capacitive return electrodes in accordance with the present disclosure.
Figure 2B:
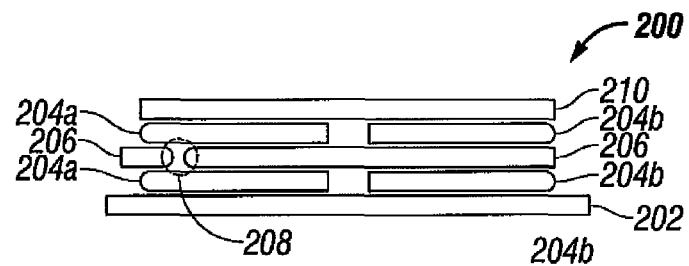
FIG. 2B is a schematic cross sectional view along line 2B-2B of the capacitive return pad of FIG. 2A in accordance with the present disclosure.

Referring now to FIGS. 2A and 2B, a capacitive return pad 200 is shown that can provide a portion of a return path for electrosurgical energy according to an embodiment of the present disclosure. Capacitive return pad 104 of FIG. 1 may be capacitive return pad 200. While capacitive return pad 200 is depicted as having a general rectangular shape, it is within the scope of the present disclosure for capacitive return pad 200 to have any suitable regular or irregular shape.

Capacitive return pad 200 includes backing layer 202 with capacitive return electrodes 204A and 204B disposed thereon, each having two lawyers of foil with dielectric layer 206 disposed therebetween (see FIG. 2B). Dielectric layer 206 is indicated by a dashed-line outline. Dielectric layer 206 provides the electrical insulation between the metal foils of each of capacitive return electrodes 204A and/or 204B making them "capacitive". Dielectric layer 206 allows high frequency electrosurgical energy to pass to a patient but prevents low frequency and DC current from passing through dielectric layer 206 to the patient. Conductive layer 210 provides low impedance contact between the bottom layer of foil of each of capacitive return electrodes 204A and 204B and the tissue of the patient, e.g., patient P of FIG. 1, during electrosurgery. (Conductive layer 210 is shown as being transparent in FIG. 2A).

The dielectric layer 206 can be damaged and/or may have a manufacturing defect. For example, a knife may accidentally pierce through dielectric layer 206 thus causing the two layers of foil of one of capacitive return electrodes 204A or 204B to have direct (e.g., non-capacitive) electrical contact with each other causing a fault. The fault can cause localized excessive heating in the region where the dielectric is pierced. The shorting of the two metal layers (e.g., foil) can cause a phase shift.

A fault may also be caused by incomplete dielectric material between the two foils of each of capacitive return electrodes 204A and/or 204B, e.g., from detects in dielectric layer 206. Fault 208 is shown as existing in capacitive return pad 200. Fault 208 is shown as a pinhole defect in dielectric layer 206 causing the two foil layers of capacitive return electrode 204A to contact each other. In FIG. 2B, fault 208 is viewable as a cross section along line 2B-2B of FIG. 1 that crosses fault 208. Note that in FIGS. 2A and 2B, fault 208 is caused by the absence of dielectric layer 206 in a specific localized region exposing the two foil layers of capacitive return electrode 204A such that they have direct electrical contact with each other. This causes the capacitive return pad 200 to have less capacitance (or none) as compared to a capacitive return pad without a fault. By monitoring the electrosurgical energy, an electrosurgical generator can detect a fault, such as one caused by pinhole defect 208 (discussed in more detail below).

Capacitive return pad 200 may include additional layers not depicted; for example, a heat distribution layer, a layer for monitoring circuitry or components, a passive cooling layer, an active cooling layer, an insulating layer, an attachment layer, and/or the like may also be include. The attachment layer may be disposed on a patient-contacting surface of capacitive return pad 200 and may be formed from an adhesive material (not explicitly shown) which may be, but is not limited to, a polyhesive adhesive, a Z-axis adhesive, a water-insoluble, hydrophilic, pressure-sensitive adhesive, or any combinations thereof, such as POLYHESIVE™ adhesive manufactured by Valleylab, a division of Covidien (formerly Tyco Healthcare) of Boulder, Colo. The adhesive is preferably conductive; however, it is within the scope of the present disclosure to include dielectric layers and/or portions thereof. The attachment layer ensures an optimal surface contact area between the capacitive return pad 200 and the patient "P," which minimizes the risk of damage to tissue.

Backing layer 202 supports a pair of split capacitive return electrodes 204A and 204B for positioning on tissue of a patient during electrosurgery. Backing layer 202 may be made of cloth, cardboard, woven or non-woven material, or any suitable material. In one embodiment, backing layer 202 may be formed from a dielectric material such as flexible polymer materials to enhance capacitive properties of the capacitive return pad 200. The polymer materials may be polyimide film sold under a trademark KAPTON™ and polyester film, such as biaxially-oriented polyethylene terephthalate (boPET) polyester film sold under trademarks MYLAR™ and MELINEX™. In another embodiment, backing layer 202 may act as an insulating layer between the pair of split capacitive return electrodes 204A and 204B and an attachment layer (not depicted).

The capacitive return electrodes 204A and 204B may be made from materials that include aluminum, copper, mylar, metalized mylar, silver, gold, stainless steel or other suitable conductive material, may be of various shapes, and may be arranged in various configurations and orientations. The split configuration of the capacitive return electrodes 204A and 204B create a measurable capacitance therebetween which may be measured by electrosurgical generator 102 (see FIG. 1) to determine adherence of the electrosurgical return pad 200 to the patient "P." Also, the current flowing through each (or multiple) foil(s) of capacitive return electrodes 204A and/or 204B can be monitored to determine the degree of adherence.

More specifically, capacitive coupling between the split return electrodes 204A and 204B increases upon the initial placement of the capacitive return pad 200 in contact with the patient "P." This capacitance corresponds to full adherence of the capacitive return pad 200 to the patient. During the procedure, capacitive return pad 200 may peel from the patient "P," thereby decreasing the adherence factor thereof. The decrease in adherence directly affects the capacitance between the capacitive return electrodes 204A and 204B. Measuring the change in capacitance between the capacitive return electrodes 204A and 204B, therefore, provides an accurate measurement of adherence of the capacitive return pad 200 to the patient "P." The amount of capacitance coupling or the change in capacitance coupling then may be used to insure positive patient contact or to determine adequate patient coverage of the capacitive return pad 200. Other methods for monitoring contact quality of the return pad to the patient include utilizing a sensor to communicate parameters such as capacitance, to the electrosurgical generator. One such system and method of monitoring contact quality is disclosed in U.S. patent application Ser. No. 11/800,687 entitled "CAPACITIVE ELECTROSURGICAL RETURN PAD WITH CONTACT QUALITY MONITOR- ING," filed May 7, 2007. Another such system and method of monitoring contact quality is disclosed in U.S. patent application Ser. No. 12/396,814 entitled "VARIABLE CAPACITIVE ELECTRODE PAD," filed Mar. 17, 2008.

Figure 3A:
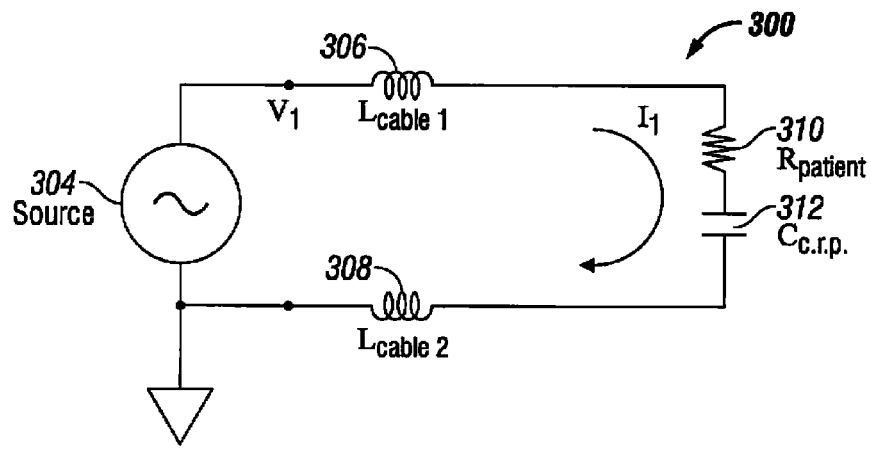
FIG. 3A is a circuit schematic that is an electrical approximation of an electrosurgical system when no fault exists in accordance with the present disclosure.
Figure 3B:
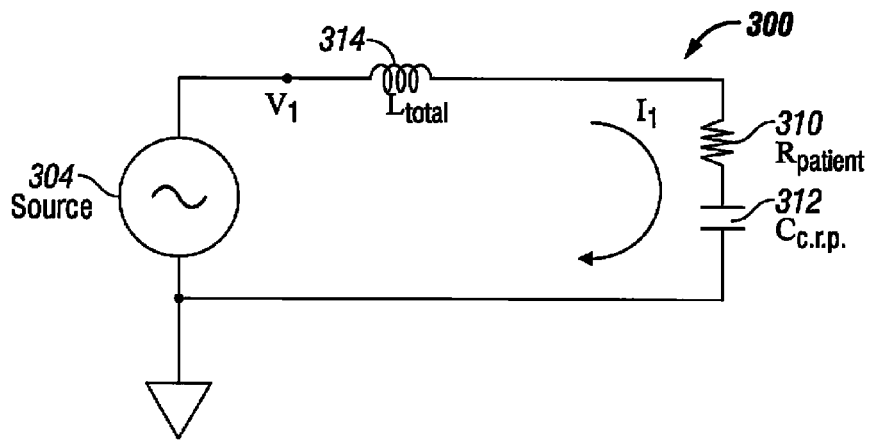
FIG. 3B is a simplified, but equivalent, circuit schematic of the circuit of FIG. 3A in accordance with the present disclosure.
Figure 3C:
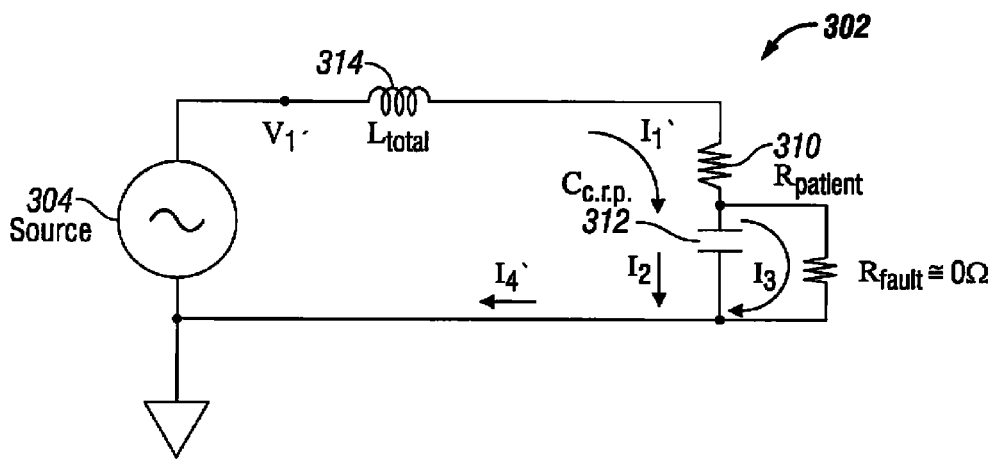
FIG. 3C is a circuit schematic that is an electrical approximation of an electrosurgical system when a pinhole fault exists in accordance with the present disclosure.

Refer to FIGS. 3A-3C for an illustration of how a fault can be detected by an electrosurgical system, e.g. electrosurgical system 100. FIG. 3A shows circuit schematic 300 that is an electrical approximation of an electrosurgical system with no fault, FIG. 3B shows a simplified, but equivalent, circuit schematic 100 of the circuit schematic of FIG. 3A, and FIG. 3C shows circuit schematic 302 that is an electrical approximation of an electrosurgical system having a fault.

Referring to FIGS. 1 and 3A, circuit 300 includes source 304 that can generate the electrosurgical energy. Source 304 may be part of electrosurgical generator 102 of FIG. 1, and approximates the behavior the hardware, software, firmware, and the like that generates the electrosurgical energy. Input impedances of source 304 have been neglected for simplicity. Circuit schematic 300 includes inductors 306 and 308, which approximate the behavior of cables 108 and 110, respectively. Inductors 306 and 308 each have an inductance value of $L_{cable\ 1}$ and $L_{cable\ 2}$ henrys (H), respectively. Resistor 310 approximates the behavior of a patient e.g., patient P of FIG. 1. Resistor 310 has a value of $R_{patient}$ ohms ($\Omega$). Capacitor 312 approximates the behavior of a capacitive return pad without a fault, e.g., capacitive return pad 104 of FIG. 1 without a fault. Capacitor 312 has a value of $C_{c.r.p.}$ farads (F).

Current $I_1$, generated by source 304, is shown and travels trough the entirety of circuit schematic 300. Voltage $V_1$ is also shown and is the voltage generated by source 304. The relationship between current $I_1$ and voltage $V_1$ is a function of the values of $L_{cable\ 1}$, $L_{cable\ 2}$, $R_{patient}$, $C_{c.r.p.}$ and the waveform generated by source 304. Specifically, the phase difference between voltage $V_1$ and current $I_1$ varies depending, inter alia, these aforementioned values. The phase difference between voltage $V_1$ and $I_1$ may be determined by an electrosurgical generator, e.g., electrosurgical generator 102 of FIG. 1, to detect a fault (discussed in more detail below when discussing FIG. 3C). Additionally, although the value of $R_{patient}$ may change, this has a minimal effect on the phase difference.

FIG. 3B is a simplification of FIG. 3A, but is considered electrically equivalent. Specifically, FIG. 3B includes inductor 314 having a value $L_{total}$ henrys (H) and is defined by equation 1 below.

$$L_{total} = L_{cable1} + L_{cable2} \tag{1}$$

Thus, inductors 306 and 308 of FIG. 3A have been replaced by inductor 314 in FIG. 3B for simplicity. It can be assumed that the inductances of the cables, e.g., cables 108 and 110, will not change significantly during electrosurgery.

Referring to FIG. 3C, schematic circuit 302 is shown and is an electrical approximation of an electrosurgical system having a fault in a capacitive return pad, e.g., electrosurgical system 100 with capacitive return pad 104 having a fault (see FIG. 1). When a fault occurs in a capacitive return pad, the capacitance is "shorted" because there is direct electrical contact between the top foil layer of the capacitive return electrode and the tissue of a patient and/or there is direct electrical contact between the two foil layers of the same capacitive return electrode. This may be represented by $R_{fault}$ that has a value near or close to zero ohms ($\Omega$). This causes current $I_2$ to be about zero amps, which causes the condition as is described by equation 2 below:

$$I'_1 \cong I'_3 \cong I'_4 \tag{2}$$

Thus, the contribution of the capacitance from a capacitive return electrode is negated because of the fault. This causes the phase difference between $I_1$ and $V_1$ to change. This phase difference can be detected by an electrosurgical generator, e.g., electrosurgical generator 102 of FIG. 1.

By detecting a change in the phase difference between voltage $V_1$ and current $I_1$ during electrosurgery, a fault may be detected. Additionally or alternatively, by detecting a phase difference between voltage $V_1$ and current $I_1$, and comparing the phase difference to a predetermined threshold, e.g., after using an interrogation signal, the fault may also be detected.

The reactance of inductance 314 (i.e., $X_L$) of circuits 300 and 302 is described by equation 3 below.

$$X_L = (2\pi F) L_{total} \tag{3}$$

F is the frequency of the electrosurgical energy. The reactance of capacitor 312 (i.e., $X_C$) is described by equation 4 below.

$$X_C = \frac{1}{2\pi F C_{r.p.e.}} \tag{4}$$

And the behavior of circuits 300 and 302 is described in terms of impedance $Z_{total}$ as shown in equation 5 below.

$$Z_{total} = \sqrt{R_{patient}^2 + (X_L - X_C)^2} \tag{5}$$

The phase angle of circuit 200 (i.e., $\theta$) is described by equation 6 below, and corresponds to the condition in which no fault exists in an electrosurgical system having a capacitive return pad, e.g., electrosurgical system 100 without a fault.

$$\theta = \tan^{-1} \frac{X_L - X_C}{R_{patient}} \tag{6}$$

However, when a fault condition does exist as is illustrated by circuit 302 of FIG. 3C, the phase angle may be described by equation 7. Note that the $X_C$ has been removed from the equation because capacitor 312 has been effectively shorted by the fault.

$$\theta = \tan^{-1} \frac{X_L}{R_{patient}} \tag{7}$$

The differing values of the phase angle (also referred to herein as "phase difference") between the current and the voltage of the electrosurgical energy may be determined and utilized in detecting a fault.

Consider the following example: assume that $R_{patient}$ has a value of 100 ohms ($\Omega$), $L_{total}$ has a value of 10 ohms ($\Omega$), and $C_{r.p.e.}$ has a value of 15 ohms ($\Omega$). By using these values, the phase angle $\theta$ may be estimated when no fault exists by using equation 6 above. The phase angle occurring when no fault exists is thus described in equation 8 below.

$$\theta = \tan^{-1} \frac{10 - 15}{100} = \tan^{-1}(-.05) = -2.86° \tag{8}$$

Therefore, in this example, the phase difference (i.e., $\theta$) is $-2.86°$ when the exemplary electrosurgical system includes a capacitive return pad without a fault, e.g., such as electrosurgical system 100 as shown in FIG. 1 without a fault existing in capacitive return pad 104.

Further, consider the case in which the same electrosurgical system as described with reference to equation 8 has a fault existing in the electrosurgical return pad. The phase difference is then described by equation 7 above and, when solved, results in a phase difference as is described by equation 9 below.

$$\theta = \tan^{-1}\frac{10}{100} = \tan^{-1}(-.1) = +5.71° \quad (9)$$

The phase difference (i.e., θ) is +5.71°. The fault can be detected by examining a change in the phase difference that occurs as the fault develops or by comparing the initial phase difference to a predetermined threshold, for example, by comparing the phase difference between the current and the voltage of an interrogation signal. Thus the difference between the phase difference without a fault vs. with a fault (i.e., Δθ) is +8.57° as is shown in equation 10 below.

$$\Delta\theta = 5.71° + 2.86° = +8.57° \quad (10)$$

Note that in this example the capacitance value is dominate, and thus the phase angle changes from a negative value to a positive value. However, consider the following second example in which the inductance is dominant: assume that $R_{patient}$ has a value of 100 ohms (Ω), $L_{total}$ has a value of 15 ohms (Ω), and $C_{r.p.e.}$ has a value of 10 ohms (Ω). By using these values, the phase angle θ may be estimated when no fault exists by using equation 6 above. The phase angle occurring when no fault exists (in this second example) is thus described in equation 11 below.

$$\theta = \tan^{-1}\frac{15-10}{100} = \tan^{-1}(-.05) = +2.86° \quad (11)$$

The phase angle occurring when a fault does exist is described by equation 12 below.

$$\theta = \tan^{-1}\frac{15}{100} = \tan^{-1}(-.15) = +8.53° \quad (12)$$

Note that the two phase angles of equations 11 and 12 are positive because the inductance is dominate. These two phase angles are in contrast to the first example in which the capacitance was dominant (as is described in equations 8, 9, and 10). Thus the difference between the phase difference without a fault vs. with a fault (i.e., Δθ) is +5.67° as is shown in equation 13 below.

$$\Delta\theta = 8.53° - 2.86° = +5.67° \quad (13)$$

As mentioned above, the determined phase difference may be compared to a predetermined threshold to detect a fault and/or the phase difference may be monitored to detect a fault in a capacitive return pad, e.g., by detecting a change in the phase difference during electrosurgery and/or by detecting an increase in the phase difference during electrosurgery.

Figure 4:
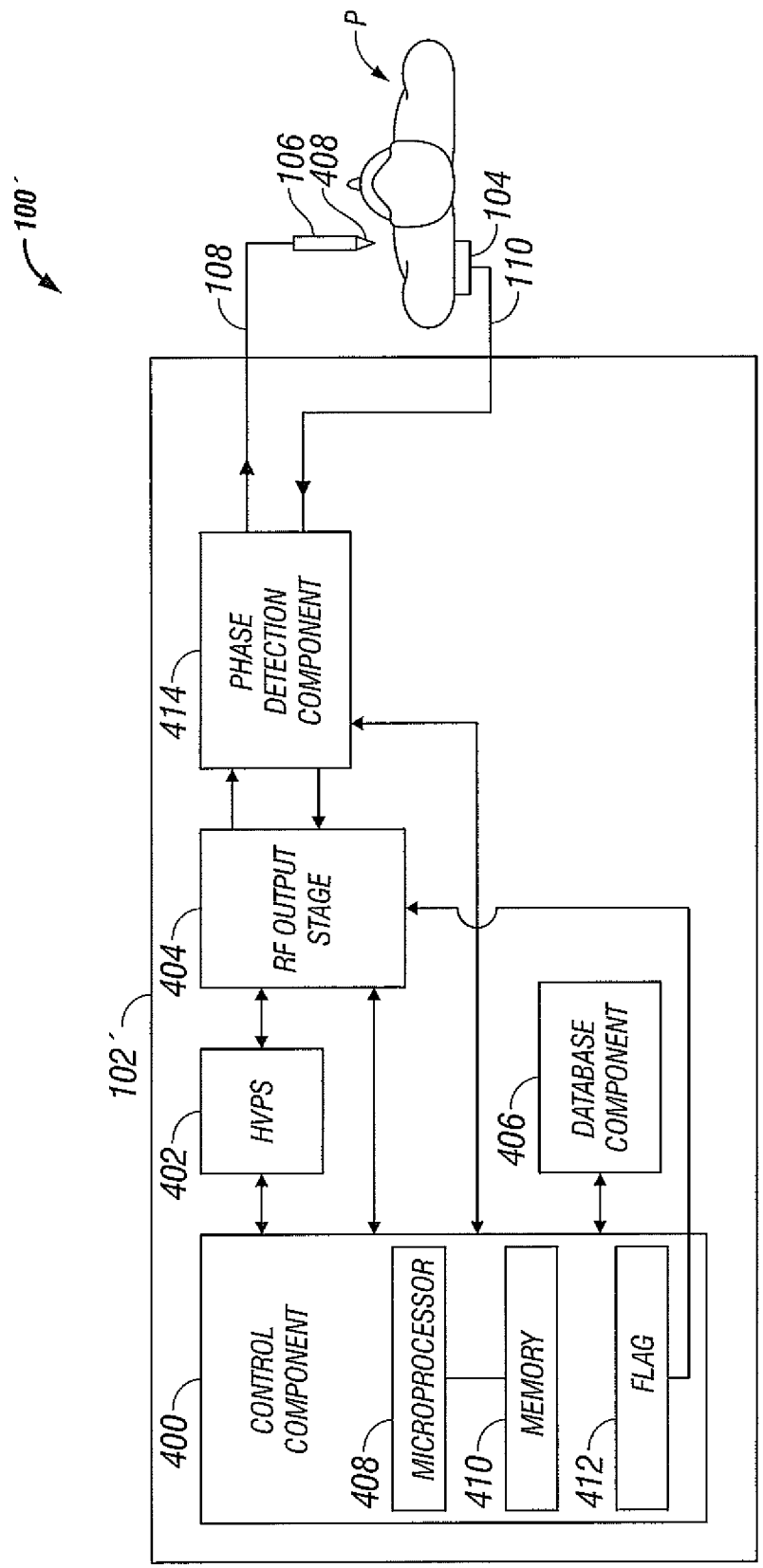
FIG. 4 is a block diagram of an electrosurgical system having an electrosurgical generator including a phase detection component and a database component in accordance with the present disclosure.

FIG. 4 shows a schematic block diagram of electrosurgical system 100' having electrosurgical generator 102'. Electrosurgical generator 102' includes a control component 400, a high voltage DC power supply 402 ("HVPS"), an RF output stage 404, a phase detection component 414, and a database component 406. HVPS 402 provides high voltage DC power to RF output stage 404, which then converts high voltage DC power into electrosurgical energy and delivers the electrosurgical energy to active electrode 408 of electrosurgical instrument 106. In particular, RF output stage 404 generates sinusoidal waveforms of electrosurgical energy. RF output stage 404 is configured to generate a plurality of waveforms having various duty cycles, peak voltages, crest factors, and other suitable parameters. Certain types of waveforms are suitable for specific electrosurgical modes. For instance, RF output stage 404 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

Control component 400 includes a microprocessor 408 operably connected to a memory 410, which may be volatile type memory (e.g., RAM) and/or non-volatile type memory (e.g., flash media, disk media, etc.). Control component additionally includes flag 412 that may be raised. Flag 412 may be a software or hardware flag, e.g., a software interrupt or a hardware interrupt, respectively. Control component 400 includes an output port that is operably connected to the HVPS 402 and/or RE output stage 404 that allows the control component 400 to control the output of electrosurgical generator 102' according to either open and/or closed control loop schemes. Control component 400 may include any suitable logic processor (e.g., control circuit), hardware, software, firmware, or any other logic control adapted to perform the calculations discussed herein.

Electrosurgical generator 102' includes a sensor circuit (not explicitly shown) having suitable sensors for measuring a variety of tissue and energy properties (e.g., tissue impedance, tissue temperature, output current and/or voltage, etc.) and to provide feedback to the control component 400 based on the measured properties. Such sensors are within the purview of those skilled in the art. Control component 400 may send signals to HVPS 402 and/or RF output stage 404, which adjust DC and/or RF power supply, respectively. Control component 400 also receives input signals from the input controls of the electrosurgical generator 102' or electrosurgical instrument 106. Control component 404 may utilizes the input signals to adjust output power, adjust the electrosurgical waveform of the electrosurgical generator 102', or perform other control functions therein. For example, control component 400 may utilize a feedback loop control algorithm such as a P-I-D control algorithm Electrosurgical generator 102' also includes phase detection component 414 that is in operative communication with control component 404. Phase detection component 414 can determine a phase difference between the current and the voltage of the electrosurgical energy travelling through patient P via electrosurgical instrument 106 and capacitive return pad 104. This phase difference may be communicated to control component 400 for detecting a fault in capacitive return pad 104. As mentioned above, control component 404 may continuously monitor the phase difference and/or compare the phase difference to a predetermined threshold to detect a fault in capacitive return pad 104.

Database component 406 can communicate the predetermine threshold to control component 400 and control component 400 may compare the predetermined threshold to the phase difference received from phase detection component 414. Database component 406 can calculate the predetermined threshold by utilizing one or more parameters, such as electrical parameters and/or physical parameters of electrosurgical system 100'. These parameters may be automatically received by database component 406 or may be manually inputted by a technician, nurse, or surgeon. Additionally or alternatively, these parameters may be initially processed by control component 400 and then communicated to database component 406. Some of the parameters may be electronically communicated to control component 400 and/or database component 406, e.g., a parameter may be communicated wirelessly such as through an RFID device.

These parameters may include a length of a cable (e.g., a length of one of cables 110 and 108), an impedance of the cable, a characteristic impedance of the cable, a resistance of the cable, an inductance of the cable, a capacitance of the cable, the age of a patient (e.g., patient P), a weight of the patient, a height of the patient, a model number of the capacitive return pad (e.g., capacitive return pad 104), a RFID interrogation of the cable, and another RFID interrogation of the capacitive return pad. An RFID interrogation may be from an RFID chip and can include data that describes a characteristic of an item. For example, capacitive return pad 104 may include an REID chip that electrosurgical generator 102' interrogates. The RFID chip embedded in capacitive return pad 104 may transmit its estimated capacitance.

As mentioned above, phase detection component 414 can continuously communicate the phase difference to control component 400, such as in analog form, digital form, using a pulse width modulated signal, using a frequency modulated signal, using an analog modulated signal, or any other suitable phase difference communication technology. Phase detection component 414 may included hardware, software, firmware, or the like to determine the phase, e.g., an analog-to digital converter, an analog multiplier, a zero crossing detector, a digital signal processor, a phase-locked-loop circuit, a sample-and-hold circuit, a phase-voltage converter having an XOR logic gate, and/or a sequential-phase detection and a current transformer.

Figure 5:
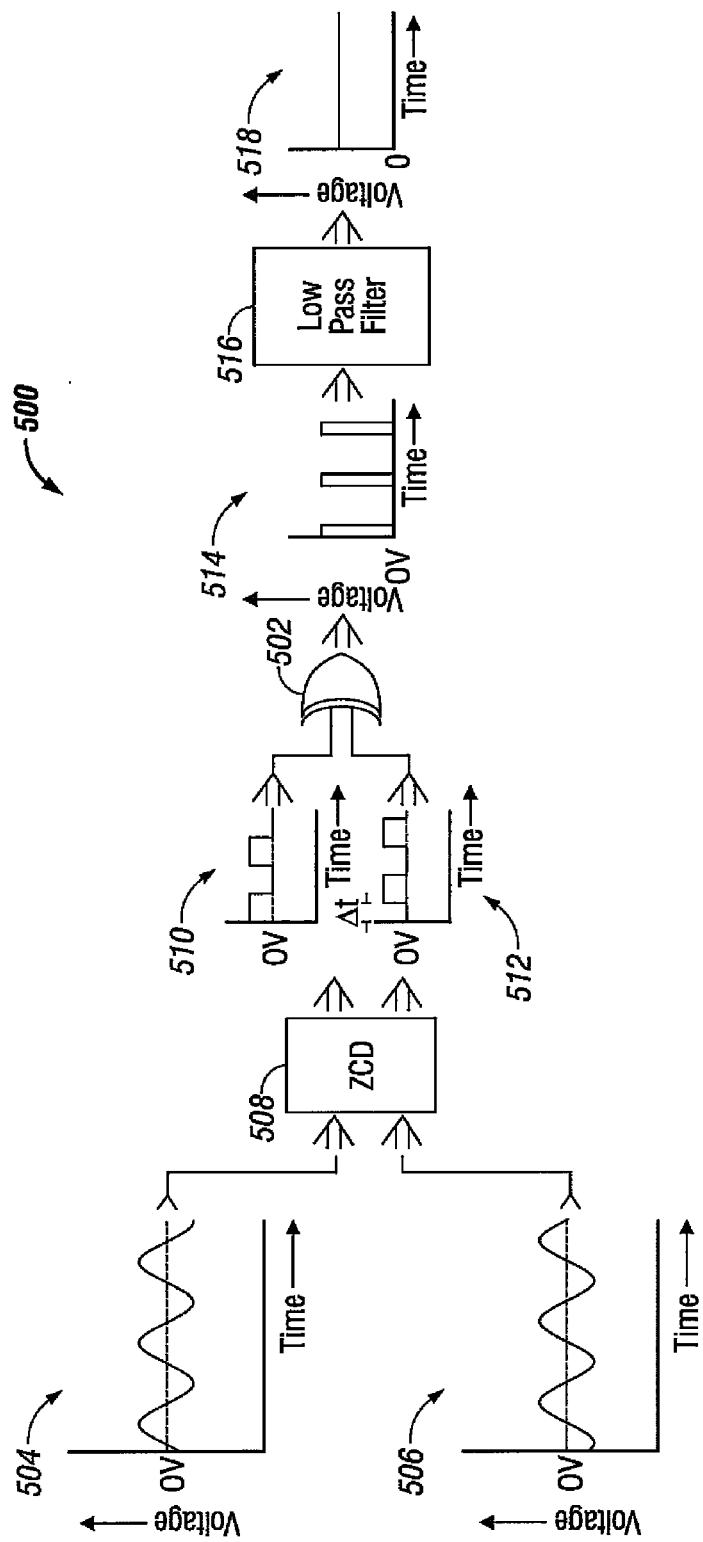
FIG. 5 is a diagram of a phase-to-voltage converter having an exclusive OR logic gate (XOR) which can facilitate determining a phase difference between current and voltage of electrosurgical energy in accordance with the present disclosure.

FIG. 5 shows a diagram 500 of one embodiment of a phase-to-voltage converter having an exclusive OR logic gate (XOR) 502 which can facilitate determining a phase difference between current and voltage of electrosurgical energy. The voltage and current waveforms of the electrosurgical energy are initially converted to representative voltage waveforms. Graph 504 illustrates a voltage waveform that is linearly related to the voltage of the electrosurgical energy. Graph 506 illustrates a voltage waveform that is linearly related to the current of the electrosurgical energy. The voltage waveforms represented by graphs 504 and 506 may be in analog or digital form, and may be created using a transformer, a current sense transformer, or any other suitable sensing circuitry. Note that the center voltage of the peak-to-peak voltage of graphs 504 and 506 is zero volts, thus the two waveforms have a zero voltage "offset".

The two waveforms of graphs 504 and 506 are inputs of zero-crossing detector ("ZCD") 508. When one of the voltage waveforms is above zero volts ZCD 508 outputs a digital "1" which is also referred to as a "HIGH". Additionally, when the respective voltage waveform is below zero volts, ZCD 508 outputs a digital "0" which is also referred to as a "LOW". For example, the digital "1" may be represented by 5 volts while a digital "0" may be represented by zero volts (i.e., TTL logical voltage levels). Graphs 510 and 512 illustrate the two waveforms after the waveforms of graphs 504 and 506 are processed by ZCD 508, respectively.

Note that the phase difference between the waveforms of graphs 504 and 506 are also present in the two waveforms of graphs 510 and 512. This phase difference is denoted in the time domain as Δt which is the time one wave is delayed (or advanced) as compared to the other. These two waveforms are inputs to exclusive OR logic gate (XOR) 502. XOR 502 produces a waveform that is represented by graph 514. XOR 502 outputs a digital "1" (or "HIGH") when the two square waves of graphs 510 and 512 differ and a digital "0" when the two square waves are logically the same, e.g., two digital "1"s result in an output of a digital "0" while a digital "1" and a digital "0" result in an output of a digital "1". This results in the duty cycle, i.e., the amount of time the waveform is high, to be directly related to the phase difference between the two waveforms of graphs 504 and 506. The waveform of graph 514 is an input of low pass filter 516, which converts the signal to a DC voltage value as shown in graph 518.

When there is no phase difference (i.e., 0°) between the waveforms of graphs 504 and 506 then the DC voltage is zero while a 180° phase difference results in the maximum possible DC voltage value. Diagram 500 illustrates one embodiment of phase detection component 414 of FIG. 4 that determines the phase difference between the current and the voltage of the electrosurgical energy.

Figure 6:
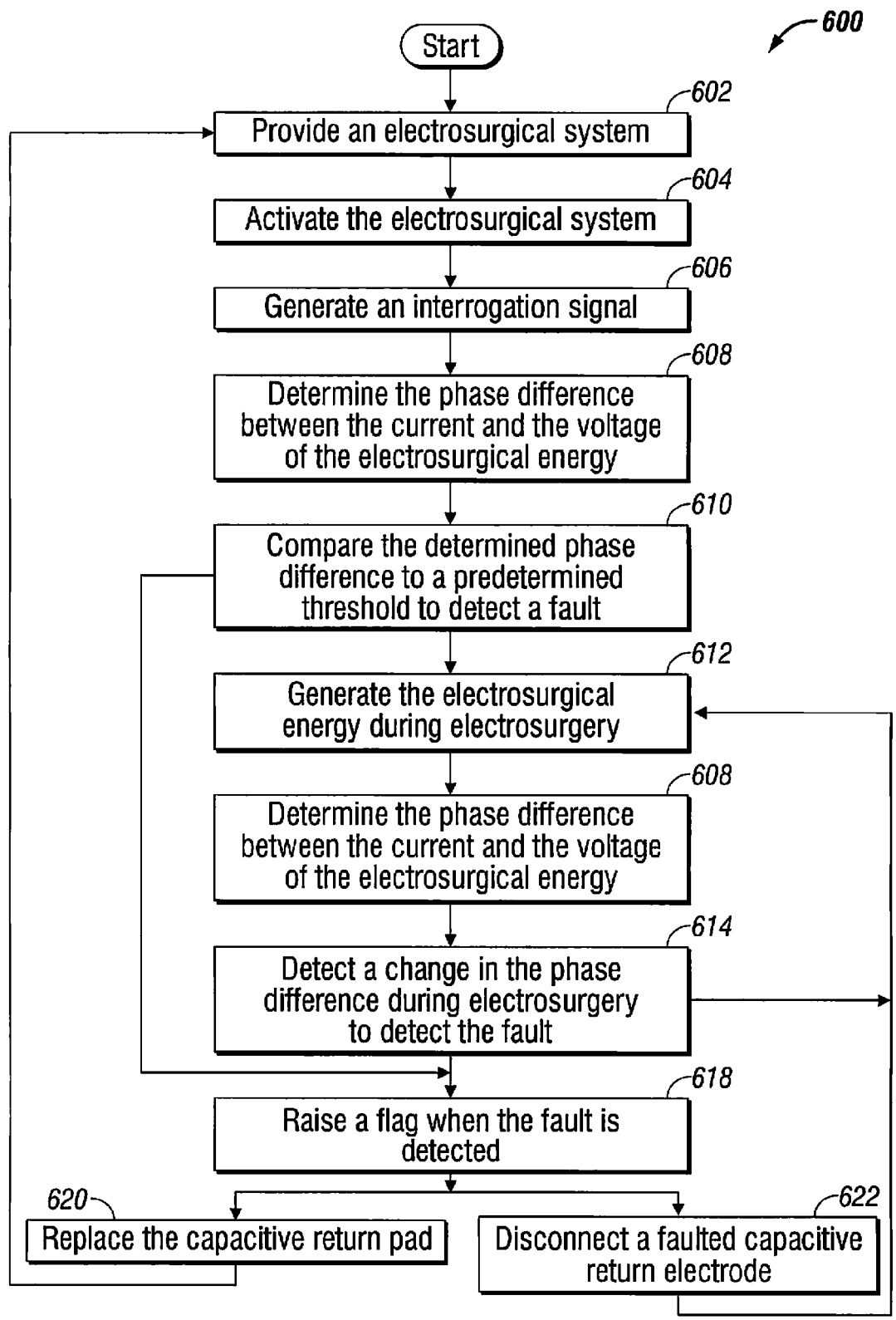
FIG. 6 is a flow chart diagram of a method for detecting a fault in a capacitive return pad in accordance with the present disclosure.

FIG. 6 is a flow chart diagram of a method 600 for detecting a fault in a capacitive return pad, e.g., capacitive return pad 104 of FIGS. 1 and 4 or capacitive return pad 200 of FIGS. 2A and 2B. Method 600 includes steps 602 through 622. Method 600 starts at step 602 that can provide an electrosurgical system such as electrosurgical system 100 of FIG. 1 or electrosurgical system 100' of FIG. 4. After providing the electrosurgical system during step 602, method 600 includes step 604 that can activate the electrosurgical system of step 602.

Step 606 can generate an interrogation signal. The interrogation signal may be similar or identical to the electrosurgical energy used during electrosurgery, e.g., the interrogation signal may be electrosurgical energy with reduced power levels and/or reduced duty cycle. The interrogation signal of step 606 may be used by step 608; step 608 can determine the phase between the current and the voltage of the electrosurgical energy, e.g. an interrogation signal.

Method 600 includes step 610 that can compare the determined phase difference, e.g., the one determined during step 608, to a predetermined threshold to detect a fault. If a fault is detected then method 600 may proceed to step 618. Step 618 can raise a flag when the fault is detected. When a fault is detected a user can replace the capacitive return pad during step 620 and restart method 600; or if the detected fault is caused by a capacitive return electrode that can be disconnected method 600 may use step 622 which can disconnect the faulted capacitive return electrode and keep the non-faulted return electrode(s) connected and operational.

Otherwise, if no fault is detected during step 610 then method 600 can proceed to step 612 that can generate the electrosurgical energy during electrosurgery. Step 608 can then determines the phase difference between the current and the voltage of the electrosurgical energy. Step 614 detects a change in the phase difference during electrosurgery to detect a fault. If no fault is detected then method 600 may proceed to step 612 to continue generation of the electrosurgical energy for use in electrosurgery. However, if a fault is detected then method 600 proceeds from step 614 to step 618, similarly to when a fault is detected during step 610.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
an electrosurgical generator configured to generate electrosurgical energy;
a capacitive return pad having at least one capacitive return electrode operatively coupled to the electrosurgical generator and configured to provide a return path for the electrosurgical energy;
a phase detection component configured to determine a phase difference between a current and a voltage of the electrosurgical energy; and
a control component in operative communication with the phase detection component and configured to receive the determined phase difference therefrom, the control component being configured to detect a short in the capacitive return pad by utilizing the determined phase difference, wherein the control component detects the short by detecting an increase in the phase difference during electrosurgery.

2. The electrosurgical system according to claim 1, wherein the short is from a pinhole defect.

3. The electrosurgical system according to claim 1, wherein:
the electrosurgical generator is further configured to generate an interrogation signal,
the phase detection component is further configured to determine a phase difference between a current and a voltage of the interrogation signal, and
the control component is further configured to detect a short in the capacitive return pad by utilizing the phase difference between the current and the voltage of the interrogation signal.

4. The electrosurgical system according to claim 1, wherein the determined phase difference is compared to a predetermined threshold to detect the short.

5. The electrosurgical system according to claim 4, wherein the electrosurgical system includes a database configured to calculate the predetermined threshold, wherein the database calculates the predetermined threshold by utilizing at least one electrical or physical parameter.

6. The electrosurgical system according to claim 5, wherein the at least one electrical or physical parameter includes at least one of a length of a cable, an impedance of the cable, a characteristic impedance of the cable, a resistance of the cable, an inductance of the cable, a capacitance of the cable, an age of a patient, a weight of the patient, a height of the patient, a model number of the capacitive return pad, a RFID interrogation of the cable, or another RFID interrogation of the capacitive return pad.

7. The electrosurgical system according to claim 1, wherein the at least one capacitive return electrode includes a plurality of capacitive return electrodes, wherein the control component disconnects a shorted capacitive return electrode of the plurality of capacitive return electrodes from the electrosurgical energy when the short is detected.

8. The electrosurgical system according to claim 1, wherein the control component detects the short by detecting a change in the phase difference during electrosurgery.

9. The electrosurgical system according to claim 1, wherein at least one of the phase detection component and the control component is at least partially implemented by an operative set of processor executable instructions configuration for execution by at least one processor.

10. The electrosurgical system according to claim 1, wherein the phase detection component includes one of an analog-to-digital converter, an analog multiplier, a zero crossing detector, a digital signal processor, a phase-locked-loop circuit, a sample-and-hold circuit, a phase-to-voltage converter having an XOR logic gate, a sequential-phase detector, or a current transformer.

11. The electrosurgical system according to claim 1, wherein the control component raises a flag when the short is detected, wherein the flag includes at least one of a software flag or a hardware flag.

12. The electrosurgical system according to claim 11, wherein the software flag is a software interrupt and the hardware flag is a hardware interrupt.

* * * * *